United States Patent
Sellers

(10) Patent No.: US 9,883,916 B2
(45) Date of Patent: Feb. 6, 2018

(54) SURGICAL SPONGE AND NEEDLE COUNTER

(71) Applicant: VARIAMED LLC, Chattanooga, TN (US)

(72) Inventor: David Sellers, Chattanooga, TN (US)

(73) Assignee: Variamed LLC, Chattanooga, TN (US)

( * ) Notice: Subject to any disclaimer, the term of this patent is extended or adjusted under 35 U.S.C. 154(b) by 0 days.

(21) Appl. No.: 15/065,177

(22) Filed: Mar. 9, 2016

(65) Prior Publication Data

US 2016/0262843 A1    Sep. 15, 2016

Related U.S. Application Data

(60) Provisional application No. 62/130,057, filed on Mar. 9, 2015.

(51) Int. Cl.

| | |
|---|---|
| *A61B 50/33* | (2016.01) |
| *A61M 5/32* | (2006.01) |
| *A61B 50/36* | (2016.01) |
| *A61B 50/37* | (2016.01) |
| *A61B 50/00* | (2016.01) |
| *A61B 50/30* | (2016.01) |
| *A61B 90/00* | (2016.01) |

(52) U.S. Cl.
CPC ............ *A61B 50/33* (2016.02); *A61B 50/362* (2016.02); *A61B 50/37* (2016.02); *A61M 5/3205* (2013.01); *A61B 2050/005* (2016.02); *A61B 2050/3006* (2016.02); *A61B 2050/3008* (2016.02); *A61B 2050/3009* (2016.02); *A61B 2050/375* (2016.02); *A61B 2090/0804* (2016.02)

(58) Field of Classification Search
CPC ......... A61B 17/06; A61B 19/02; A61B 50/33; A61B 50/36; A61B 50/362; A61B 50/37; A61B 50/3006; A61B 50/3008; A61B 50/3009; A61B 50/375; A61B 2090/0804; A61M 5/32; A61M 5/3205
USPC ....... 206/63.3, 207–210, 363–370, 438–440, 206/557–565
See application file for complete search history.

(56) References Cited

U.S. PATENT DOCUMENTS

| | | | |
|---|---|---|---|
| 3,770,119 A | 11/1973 | Hultberg et al. | |
| 3,802,555 A | 4/1974 | Grasty et al. | |
| 4,124,141 A * | 11/1978 | Armentrout | ............ B29C 65/02 206/439 |
| 4,182,448 A | 1/1980 | Huck et al. | |
| 4,190,153 A * | 2/1980 | Olsen | ..................... A61B 50/37 206/362 |
| 4,784,267 A | 11/1988 | Gessler et al. | |
| 4,832,198 A | 5/1989 | Alikhan | |
| 4,989,733 A | 2/1991 | Patry | |
| 5,316,142 A * | 5/1994 | Jain | .................. A61B 17/06061 206/370 |
| 5,372,252 A * | 12/1994 | Alexander | ............ A61M 5/001 206/210 |

(Continued)

*Primary Examiner* — Bryon Gehman
(74) *Attorney, Agent, or Firm* — Davis & Bujold PLLC; Michael J. Bujold

(57) ABSTRACT

A surgical sponge counter includes a unitary molded plastic sponge tray defining a plurality of wells each sized to hold a lap sponge. Each well has a ledge defining a recess below the sponge for collecting fluid once the sponge is replaced in the tray. A needle counting receptacle tray may be nested within the sponge tray above the sponges.

5 Claims, 7 Drawing Sheets

(56) References Cited

U.S. PATENT DOCUMENTS

| | | | | |
|---|---|---|---|---|
| 6,076,673 | A | * | 6/2000 | Fensham ................ B65D 75/32 206/210 |
| 6,622,861 | B2 | * | 9/2003 | Kissling ................ A61B 50/37 206/370 |
| 7,308,985 | B2 | * | 12/2007 | Riley ........................ A61J 1/00 206/363 |
| D569,007 | S | | 5/2008 | Koseki |
| 2002/0029989 | A1 | * | 3/2002 | Anthony .............. A61B 50/362 206/366 |
| 2004/0040873 | A1 | | 3/2004 | Koseki |
| 2004/0129591 | A1 | | 7/2004 | Koseki |
| 2011/0127188 | A1 | * | 6/2011 | Thompson .............. B32B 27/18 206/438 |

\* cited by examiner

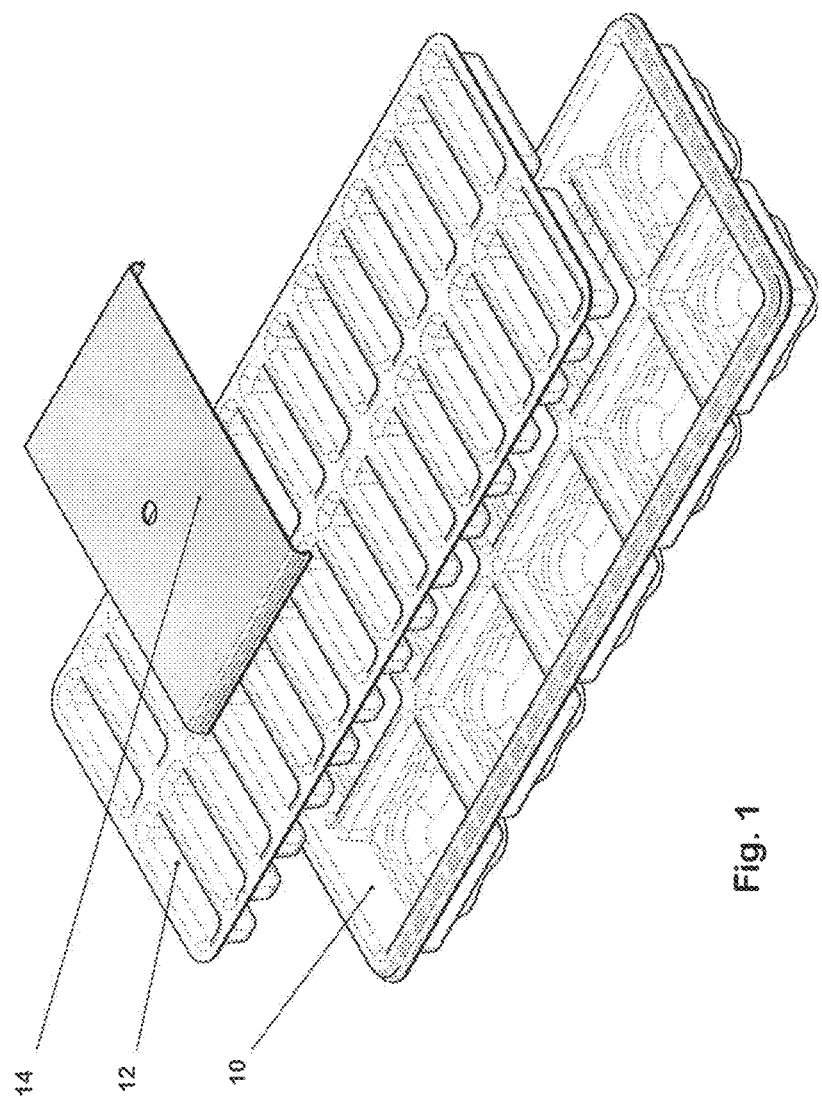

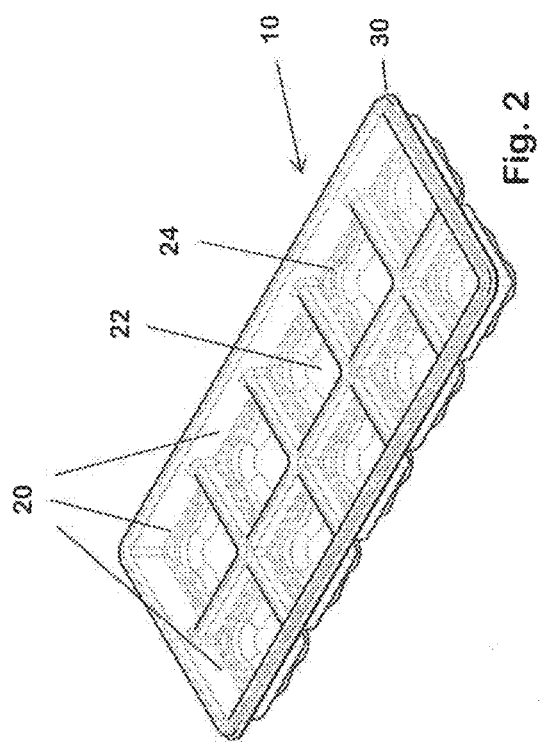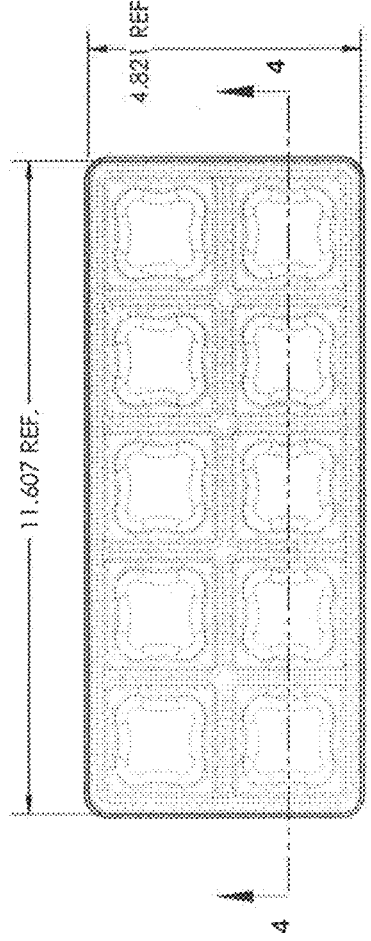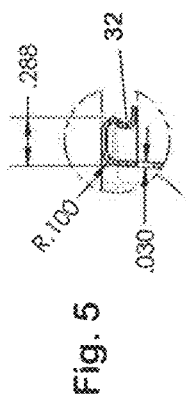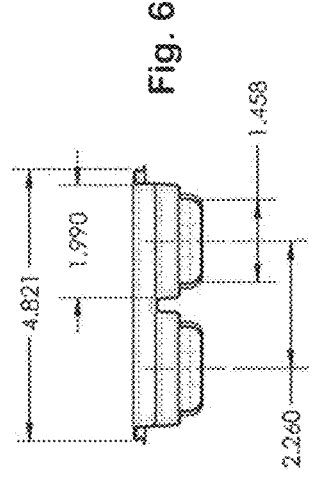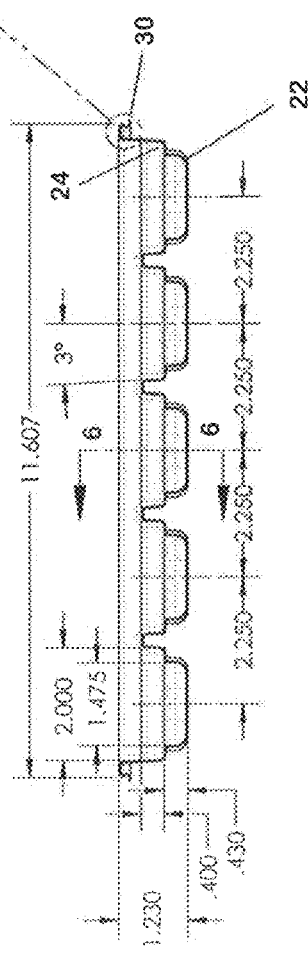

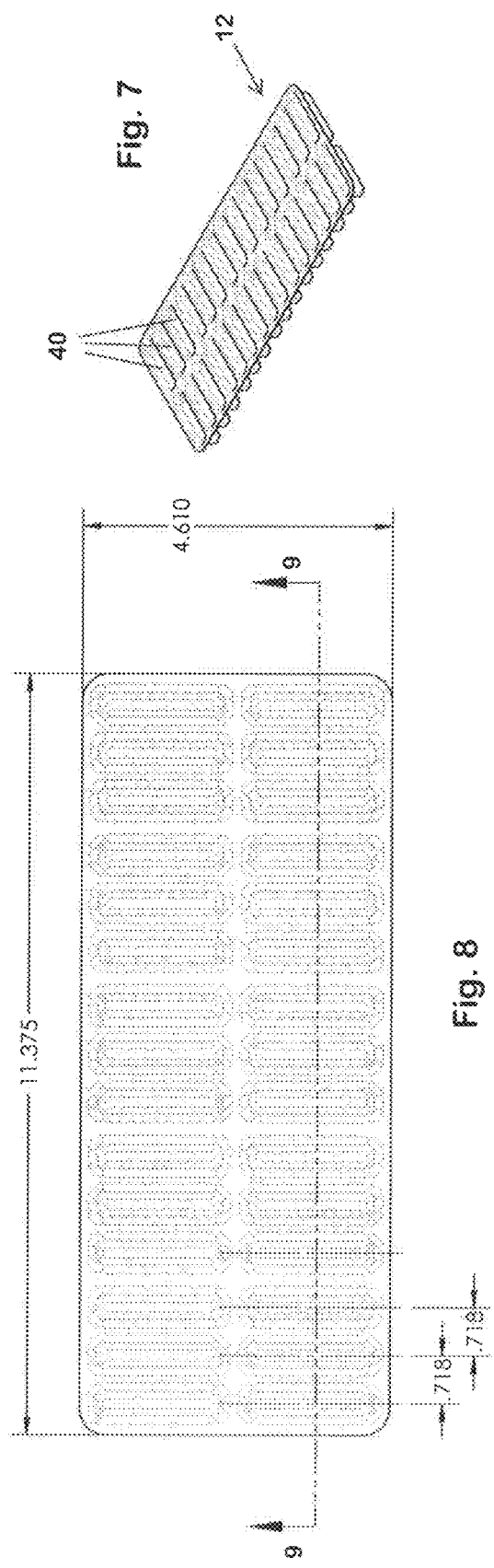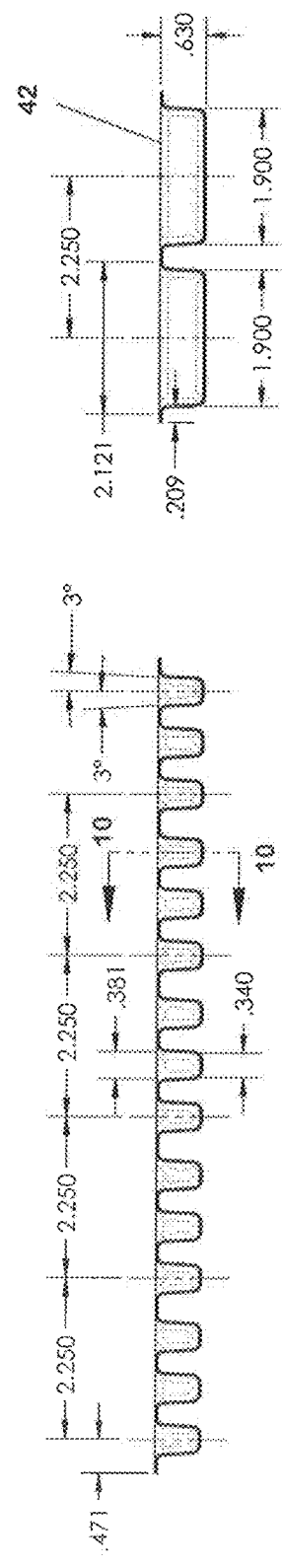

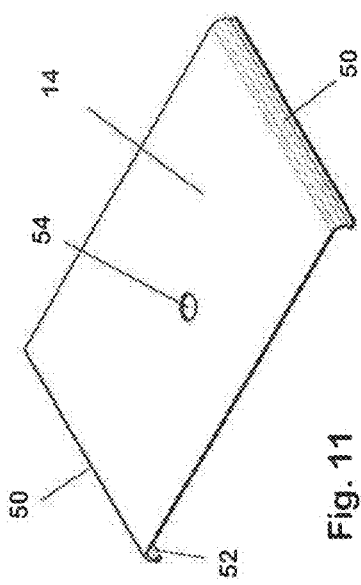
Fig. 11
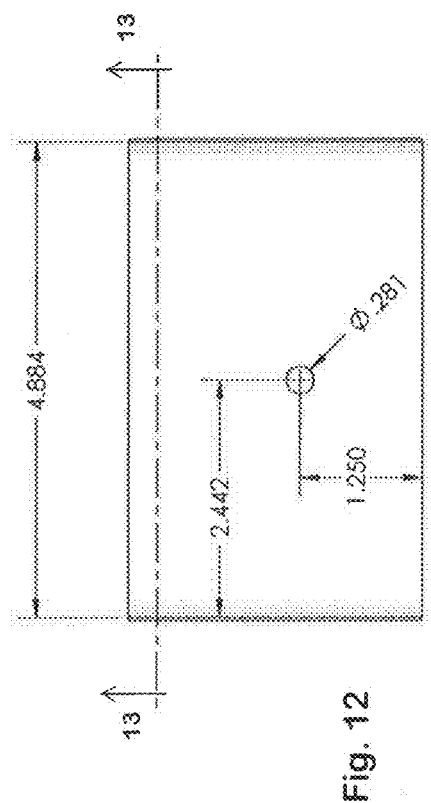
Fig. 12
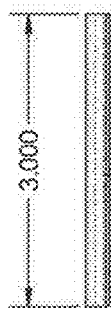
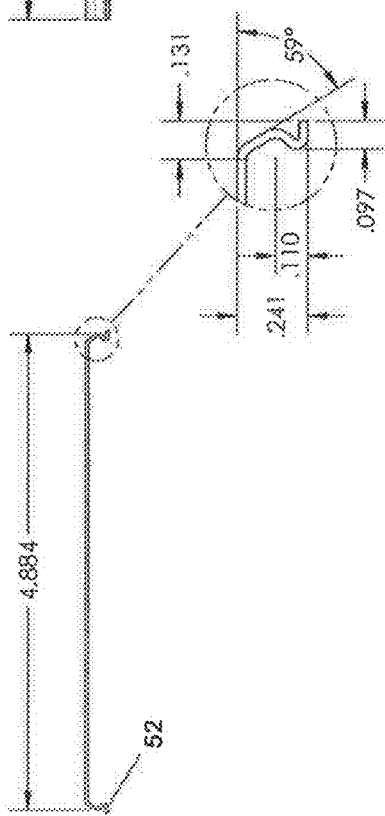
Fig. 13
Fig. 14
Fig. 15

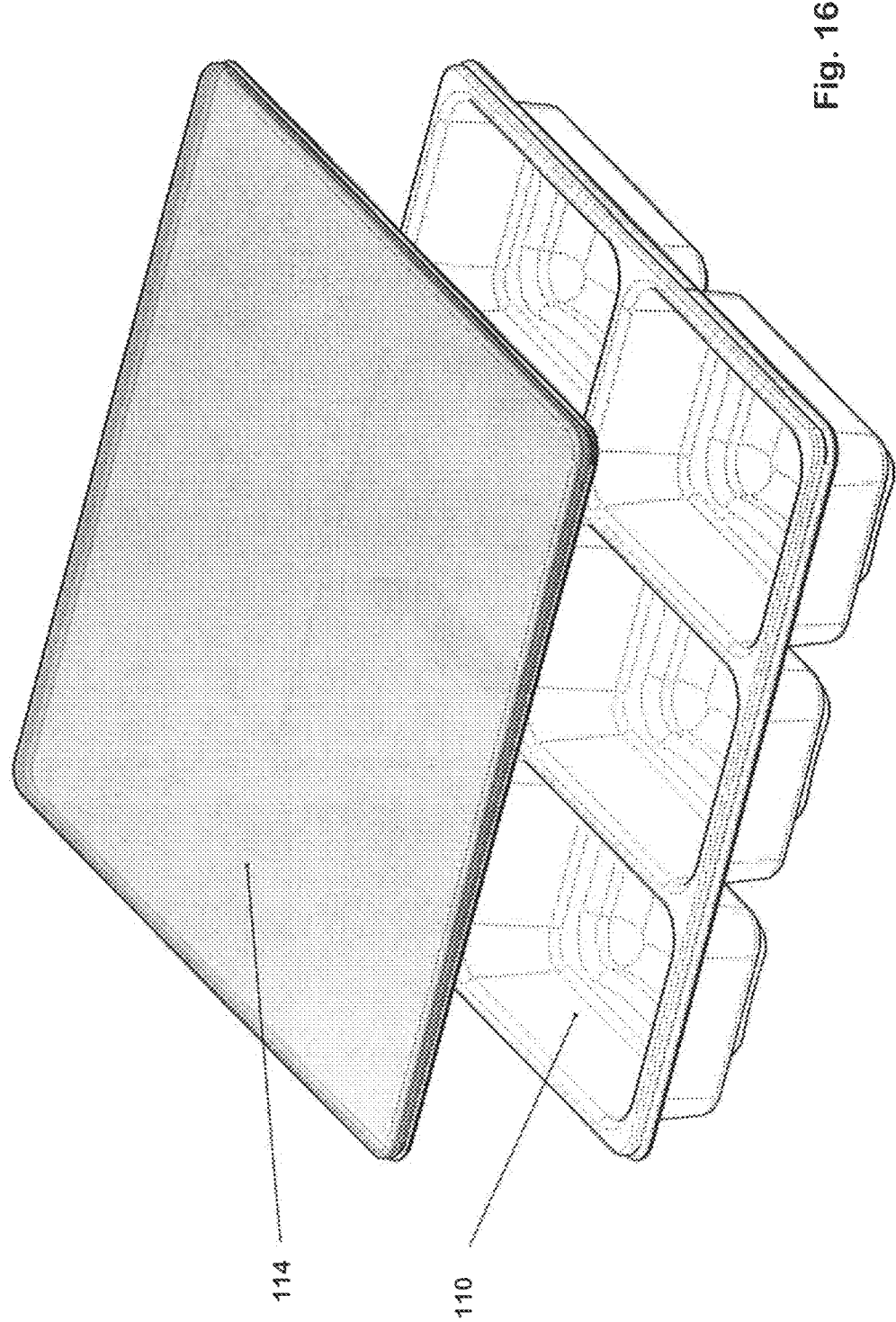

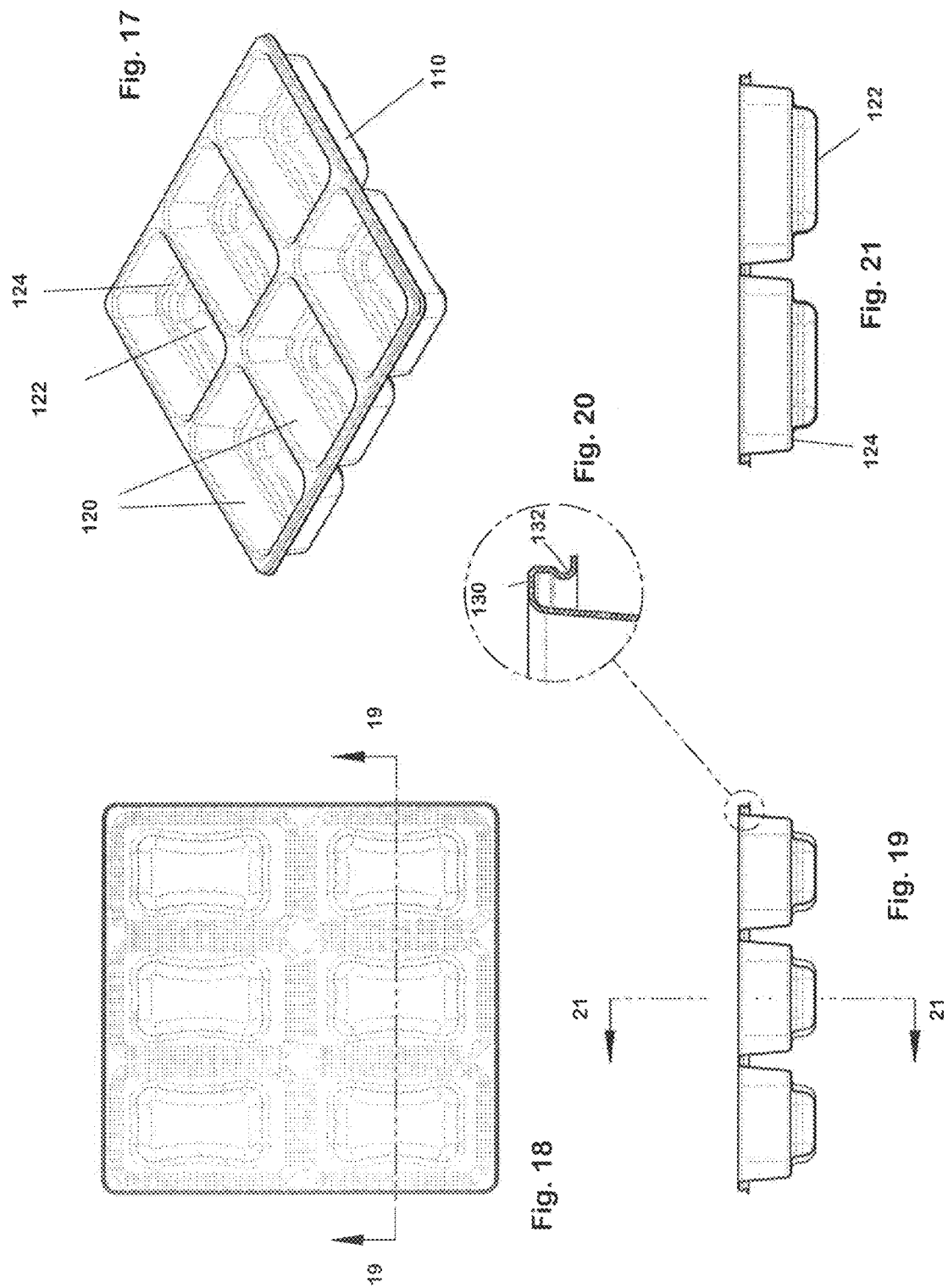

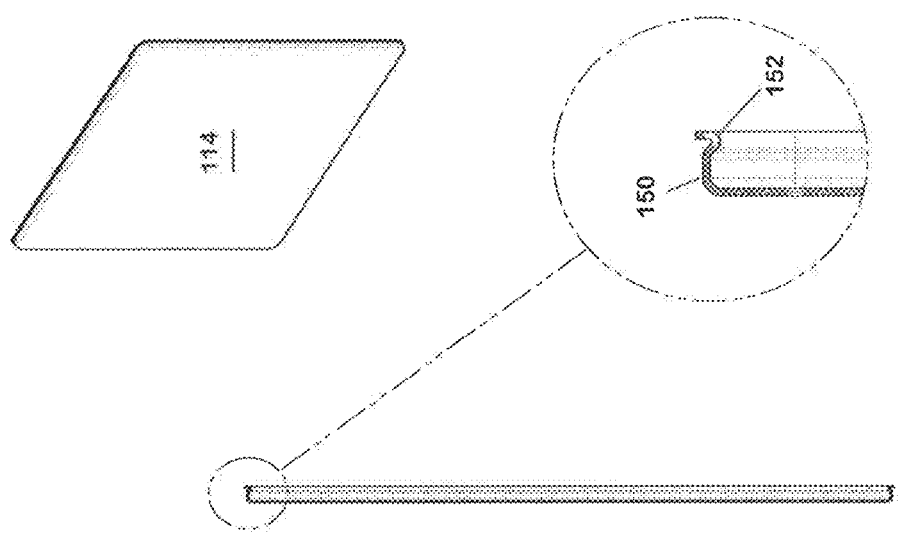
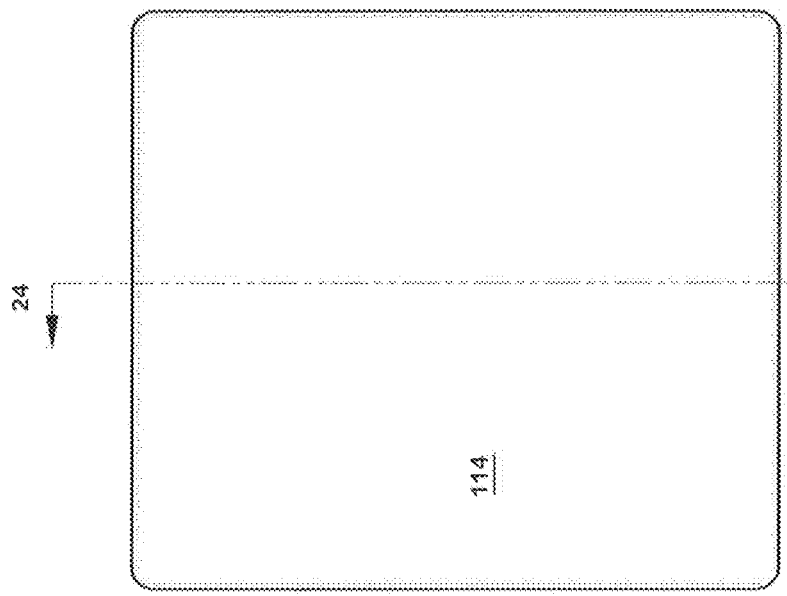

SURGICAL SPONGE AND NEEDLE COUNTER

This application claims benefit of provisional patent application 62/130,057, filed Mar. 9, 2015.

BACKGROUND OF THE INVENTION

This invention relates to a surgical sponge and needle container.

Frequently, sponges are piled onto a table or into a container during an operation. Post procedure, medical personnel attempt to count, the sponges. The sponges can hind to one another, causing a miscount.

It has been reported that seventy-four percent of all needle/sharps injuries occur as a result of passing a needle/sharp. Some form of "safety zone" for sharps is required by the joint commission in every facility.

Whenever a miscount of needles/sharps or sponges occurs, a lengthy process must be performed to insure there is no URFO (unintended retention of foreign objects). This is a time consuming process costing the facility money and the surgeon valuable time.

This invention aims to help medical personnel avoid sharps injuries, and get a proper count of sharps and sponges used in an operation.

SUMMARY OF THE INVENTION

An object of the invention is to improve the safety of surgical procedures by making it easier for surgeons and technicians to keep an accurate count of needles and sponges.

Another object of the invention is to improve needle handling safety by maintaining a safety zone around each sharp.

These and other objects are attained by a surgical sponge and needle container as described below.

This product addresses both surgical counts and needle count issues and provides a safer and more cost effective surgical environment not only for the surgeon and technical assistants, but also for the patient and the facility.

BRIEF DESCRIPTION OF THE DRAWINGS

In the accompanying drawings,

FIG. 1 is an exploded perspective of a first embodiment of the invention, showing a hypo holder, a sponge tray and a needle tray;

FIG. 2 is a perspective view of the sponge tray shown in FIG. 1;

FIG. 3 is a top plan view thereof;

FIG. 4 is a sectional view taken on the line 4-4 in FIG. 3;

FIG. 5 is an enlarged portion of FIG. 4;

FIG. 6 is a sectional view taken on the line 6-6 in FIG. 4;

FIG. 7 is a perspective view of the needle tray shown in FIG. 1;

FIG. 8 is a top plan view thereof;

FIG. 9 is a sectional view taken on the line 9-9 in FIG. 8;

FIG. 10 is a sectional view thereof, taken on the line 10-10 in FIG. 9;

FIG. 11 is a perspective view of the .hypo holder shown in FIG. 1;

FIG. 12 is a top plan view thereof;

FIG. 13 is a sectional view thereof, taken on the line 13-13 in FIG. 12;

FIG. 14 is an enlarged portion of FIG. 13; and

FIG. 15 is a side view of the holder.

FIG. 16 is an exploded perspective view of a second embodiment of the invention;

FIG. 17 is a perspective view of a sponge tray shown in FIG. 16;

FIG. 18 is a top plan view thereof;

FIG. 19 is a sectional view thereof, taken on the line 19-19 in FIG. 18;

FIG. 20 is an enlarged portion of FIG. 19;

FIG. 21 is a sectional view thereof, taken on line 21-21 in FIG. 19;

FIG. 22 is a perspective view of a "safety zone" lid shown in FIG. 16;

FIG. 23 is a top plan view thereof;

FIG. 24 is a sectional view thereof, taken on the line 24-24 in FIG. 23; and

FIG. 25 is an enlarged portion of FIG. 24.

DESCRIPTION OF TWO PREFERRED EMBODIMENTS

A first embodiment of the invention is shown in FIGS. 1-15.

The counter comprises a sponge tray 10, a needle tray 12 which nests in the sponge tray, and a cover 14 over the needle tray. These elements are initially held together by a shrink-wrap band at the perimeter of the trays.

The sponge tray 10 (FIGS. 2-6) is a unitary molded plastic tray defining ten wells 20. The tray initially contains ten lap sponges (not shown), one in each well. After a sponge is used, the tech should replace it in a well.

Each well 20 has a recess 22 at the bottom to receive fluids, as described below. Each recess is smaller than the sponge-receiving portion of the well, so there is a ledge 24 extending around each recess. The sponges rest on the ledges, above the recesses.

The sponge tray 10 has a peripheral flange 30 which reinforces the tray. The flange is formed so as to define a groove 32 extending along the outer periphery of the tray.

The sponge tray is substantially transparent, so that a tech can perform a quick and accurate post-surgical count of sponges. The needle tray is substantially transparent as well, to facilitate the post-surgical counting of needles.

The tech and circulating nurse can quickly perform a pre- and post-op count of the ten 4"×4" sponges. The recesses formed at the bottom of the wells, below the sponges, allow anesthetists to perform a blood loss check based on the amount of fluid in the bottom of the depression.

The needle tray 12, shown in detail in FIGS. 7-10, defines thirty wells 40 that are covered with a plastic (e.g., cellophane) film 42, Each well is numbered so that the tech can perform an accurate post-surgical needle count.

The needle tray is sized to nest within the upper portion of the sponge tray, and in the embodiment show, lacks a peripheral flange. The needle tray covers the sponges until it is removed from its nested position within the sponge tray.

In use, when the surgeon is finished with a sharp, he or she places it in the safety zone. The tech can then retrieve the sharp from the safety zone and with it, puncture the cellophane. The sharp drops into the well, removing this item from the operating field, which reduces the possibility of a sharps injury. The needle wells also make for an accurate post-op count of all sharps used during the procedure.

Element 14 (FIGS. 11-15) is a hypo (hypodermic needle) holder, which measures about three inches by five inches. The holder is a generally flat plate, with flanges 50 formed along two opposed sides of the plate. The flanges 50 are formed as seen in FIG. 14, to provide beads 52 which can snap into the groove 32 at the periphery of the sponge tray. When installed, the hypo holder securely clamps the needle and sponge trays together, forming a single unit which is easily removed from the surgical pack.

As seen in FIG. 11, the hypo holder 14 has at least one hole 54 for receiving a hypodermic needle with its cap on. The needle cap—when inserted into the hypo holder—creates a stand for the hypodermic needle. The hypo holder also allows the tech to place a used hypodermic needle back into the cap using a two-handed method. The tech holds the hypo holder with one hand and, with the hypodermic needle in the other hand, reinserts the needle into the cap. This protects the tech from sharp injury when replacing the needle into the cap.

A second embodiment of the invention is shown in FIGS. 16-25. This embodiment also has a sponge tray 110, does not have a separate needle tray or hypo holder, instead having a lid 114 which serves as a safety zone for sharps.

The sponge tray 110 (FIGS. 17-21) is substantially transparent, so that the tech and circulating nurse can perform a pre- and post-op count of six-inch by eight-inch lap sponges used in surgical procedures. After a sponge has been used, it is replaced into the well 120 it was removed from. As with the first embodiment, ledges 124 at the bottoms of the wells 120 define reduced-size recesses 122 below the sponges. The recesses help anaesthetists perform a blood loss check based on the amount of fluid which collects at the bottom of the wells.

Since there is no needle tray in this embodiment to serve as a cover for the sponge tray, a full lid 114 is provided instead of the hypodermic needle holder. The lid is bounded by a peripheral flange 150 having a bead 152 which snaps into the groove 132 formed in the flange 130 at the edge of the sponge tray. The lid, which can serve as a "safety zone," is preferably a bright orange color, so that it can be seen better by the surgeon with his peripheral vision when placing a used instrument containing a needle onto the safety zone. A tech may subsequently retrieve the instrument and any used needles from the safety zone, free of the surgeon's hand.

Some of the drawings contain dimensions. It should be understood these are presently preferred dimensions, and that the invention can be made in other sizes or proportions. Similarly, the sponge and needle trays are not limited to a particular number or shape. Those shown in the drawings are merely illustrative.

Inasmuch as the invention is subject to modification and variations, the invention should be measured not by the above examples, but rather by the claims below.

What is claimed is:

1. A combination surgical sponge counter and needle tray comprising
    a unitary molded plastic sponge tray defining a plurality of wells, each of said wells being sized to hold a respective lap sponge,
    each well having a ledge defining a recess below its respective sponge for collecting fluid once a used sponge is replaced in the tray,
    a needle tray defining plurality of wells for holding used hypodermic needles and sharps,
    said needle tray nesting within a top portion of the sponge tray, and
    a film seal covering all said wells in the needles tray, whereby needles and sharps may be inserted through the film into the wells.

2. A combination surgical sponge counter and needle tray as recited in claim 1, further comprising a cover comprising a plate with at least one hole therein for holding a hypodermic needle cap.

3. A combination surgical sponge counter and needles tray as recited in claim 2, wherein said plate has two opposed edges with flanges formed thereon, each of said flanges having a bead which snaps over a peripheral edge of the sponge tray to hold the cover and the sponge tray together as an assembly.

4. A combination surgical sponge counter and needle tray as recited in claim 3, wherein the peripheral edge of the sponge tray has a peripheral flange formed thereon, said peripheral flange forming a groove for receiving the beads of the flanges.

5. A combination surgical sponge counter and needle holder as recited in claim 1, wherein both the sponge tray and the needle tray are transparent.

* * * * *